United States Patent [19]

Hara et al.

[11] 4,155,942

[45] May 22, 1979

[54] PROCESS FOR THE PRODUCTION OF ORGANOALKALI METALS

[75] Inventors: Hajime Hara, Fujisawa; Atsushi Kaiya; Yoshihiko Araki, both of Kawasaki, all of Japan

[73] Assignee: Nippon Oil Company, Limited, Tokyo, Japan

[21] Appl. No.: 859,844

[22] Filed: Dec. 12, 1977

[30] Foreign Application Priority Data

Dec. 16, 1976 [JP] Japan .................................. 51-150340

[51] Int. Cl.$^2$ ........................... C07F 1/00; C07F 1/02; C07F 1/04; C07F 1/06
[52] U.S. Cl. ................................................. 260/665 R
[58] Field of Search ............................ 260/665 R, 389

[56] References Cited

U.S. PATENT DOCUMENTS

| | | | |
|---|---|---|---|
| 2,377,779 | 6/1945 | Hanford et al. | 260/665 R X |
| 3,090,819 | 5/1963 | Foster | 260/665 R |
| 3,278,617 | 10/1966 | Kahle et al. | 260/665 R |

OTHER PUBLICATIONS

Mallan et al., Chem. Revs. V69, pp. 693, 694, and 698–702, (1969).
Gilman et al., Organic Reactions V8, pp. 284–287, (1954).
Benkeser et al., Chem. Revs., V57, pp. 867 and 870 to 876, (1957).
Wakefield, The Chemistry of Organolithium Compounds, Pergamon Press, N.Y., pp. 26 to 28 & 66 & 67, (1974).

*Primary Examiner*—Helen M. S. Sneed
*Attorney, Agent, or Firm*—Bucknam and Archer

[57] ABSTRACT

A process of transmetalating organoalkali metals is disclosed, wherein organoalkali metal compounds are reacted with hydrocarbon compounds in the presence of predetermined amounts of oxygen.

3 Claims, No Drawings

PROCESS FOR THE PRODUCTION OF ORGANOALKALI METALS

BACKGROUND OF THE INVENTION

1. Field of the Invention

This invention relates generally to the production by transmetalation of organoalkali metals.

2. Prior Art

Organoalkali metal compounds are well known for their excellent performance as catalysts for the polymerization of olefins and diolefins and as intermediate for the synthesis of various organometallic compounds.

The principles of transmetalation contemplated hereunder may be represented by the formula:

$$R^{\oplus}M^{\ominus} + R'H \rightleftarrows R'^{\oplus}M^{\ominus} + RH$$

where M is an alkali metal and R and R' are the respective hydrocarbon residues.

The above reaction is analogous to an acid-base reaction wherein a salt of a weak acid $R^{\oplus}M^{\ominus}$ is reacted with a strong acid R'H to form a salt of a strong acid and a weak acid, respectively. This reaction is utilized for the determination of the order of acidity of hydrocarbon compounds, reference here being made to the review of Avery A. Morton appearing on the Chemical Reviews, 35 (1944), from which it is known that the greater is the disparity in acidity between R'H and RH, the easier is the transmetalation.

However, considerable difficulties have been encountered with transmetalation where the difference in acidity between R'H and RH is relatively small, in which instance extremely severe reaction conditions are required.

SUMMARY OF THE INVENTION

Whereas, it is the primary object of the present invention to provide an improved process for the production of organoalkali metals at increased yield.

It is another related object of the invention to provide an improved process which will enhance transmetalation under relatively mild reaction conditions even where the disparity in acidity between R'H and RH is small.

It has been ascertained in the course of continued research on the reaction of transmetalation that oxygen has a striking effect on the speed of such reaction as hereinafter more fully described.

Briefly stated, the process according to the invention comprises transmetalation between organoalkali metal compounds represented by the general formula:

RM where R is a hydrocarbon residue having a carbon number of 1 to 20 and a pKa value of RH exceeding 21, and M is an alkali metal selected from the group consisting of sodium, potassium, rubidium and cesium; and hydrocarbon compounds represented by the general formula:

R'H where R' is an organic residue having a carbon number of 1 to 20 and a pKa value of R'H exceeding 21 but lower than the pKa value of RH, characterized by the addition of oxygen in an amount of 0.01 to 10 mol % based on the organoalkali metal compounds, whereby organoalkali metals of the general formula R'M is produced.

The invention will be described in fuller detail with reference to the following embodiments.

DETAILED DESCRIPTION OF THE PREFERRED EMBODIMENTS

The organoalkali metal compounds employed in accordance with the invention are represented by the general formula RM where M is an alkali metal selected from the group of sodium, potassium, rubidium and cesium, and R is a hydrocarbon residue of 1 to 20 carbon atoms such as for example an alkyl group, an aryl group and an alkaryl group and having a pKa value of RH (which is a compound having hydrogen attached to the hydrocarbon residue) exceeding 21. pKa here is obtained from the equation:

$$pKa = -\log[R\oplus] \times [H\ominus]/[RH]$$

in the dissociation of $RH \rightleftarrows R\oplus + H\ominus$.

The above-defined organoalkali metal compounds are readily available from the reaction of halogenated hydrocarbons with alkali metal compounds, typical examples of such reaction products being butylsodium, amylsodium, phenylsodium, butyllithium, butylpotassium, and diphenylmethylpotassium.

The hydrocarbon compounds according to the invention are represented by the general formula R'H where R' is a hydrocarbon residue having a carbon number of 1 to 20 such as an alkyl group, an aryl group and an alkaryl group, and a pKa value of R'H exceeding 21. Typical examples of such hydrocarbon compounds include toluene, xylenes, cumene, diphenylmethane, triphenylmethane, fluorene and indene.

Needless to say, for the reaction to proceed as desired, the pKa value of the compound RH should be greater than that of the compound R'H.

Reaction temperature varies with the difference in acidity between RH and R'H. With increased acidity difference, the reaction can progress fast enough even at room temperature. Conversely, with reduced acidity difference, the reaction temperature must be raised. This temperature usually is in the range of 0° to 150° C., preferably 20° to 100° C.

There may be used inert solvents in the process of the invention, but no such solvents are required where the starting R'H compounds are liquid at reaction temperature. When inert solvents such as hydrocarbon solvents are to be used, the pKa value of the solvent should be greater than that of RH constituted by the hydrocarbon residues of the organoalkali metals. The starting hydrocarbons and the solvents should be preferably well dried with use of silica alumina or other desiccants usually used for hydrocarbons.

As previously stated, the transmetalation reaction can be effected at increased rate of speed with high yields of the intended organoalkali metals by the addition of oxygen. This oxygen may be absolutely pure, but for the sake of operating safety, it should be preferably in the form of air or a gaseous mixture of pure oxygen and pure nitrogen. The oxygen thus defined may be dissolved in the hydrocarbon or solvent to be assigned to the reaction system. It has been found that only small amounts of oxygen are required to advance the desired transmetalation reaction to completion. Excess oxygen would result in decomposed organoalkali metals or other objectionable side reactions and would further involve the danger of explosion.

It has now been found that the amount of oxygen to be used in the transmetalation process of the invention should be from 0.01 to 10 mol %, preferably from 0.5 to 5 mol %, based on the starting organoalkali metal compounds.

There is no particular limitation imposed on the pressure to be employed in the process of the invention. It may be from 0 to 100 atmospheric pressure, standard pressure or vapor pressure developed in the reaction systems at reaction temperature.

The invention will be further illustrated by way of the following examples.

Inventive Examples 1, 2 and 3, and Comparative Example 1

To nitrogen-purged and dried 500 c.c. autoclave were charged 269 c.c. of dry benzene containing 0.182 mol of phenylsodium, followed by the addition of 0.265 mol toluene and oxygen in the specific amounts listed in the following table. The reaction was effected at 80° C., and there was obtained benzylsodium. In order to examine the reaction speed in each of the Examples, samples were taken 10 minutes after raising the temperature and analyzed to reveal the results tabulated below.

|  | Amount of Air ($O_2$ in mol % based on Phenylsodium) | Yield of Benzylsodium (%) |
|---|---|---|
| Comparative Example 1 | 0 | 13 |
| Inventive Example 1 | 0.2 | 25 |
| Inventive Example 2 | 0.4 | 34 |
| Inventive Example 3 | 0.8 | 42 |

The above data is a clear evidence of the distinct advantages of the present invention that remarkably high yields of benzylsodium are obtainable by transmetalation with the supply of predetermined amounts of oxygen.

Inventive Example 4

To a 500 c.c. autoclave were charged, under nitrogen stream, 105 c.c. sodium dispersion containing 0.4 mol sodium and benzene (dispersant), 0.918 mol toluene and 172 c.c. benzene. With reaction temperature maintained at 25° to 30° C., 0.178 mol monochlorobenzene was added in droplets over about an hour, and for approximately 15 minutes thereafter, the reaction temperature was set at 30° C., followed by the charge into the autoclave of a gas containing pure oxygen and pure nitrogen at a ratio of 1:9. The amount of oxygen added corresponded to 1 mol % of phenylsodium. The temperature was increased up to 70° C. with a lapse of about 3 minutes. The yield of benzylsodium determined 10 minutes after the temperature was raised, was 76%. Whereas, benzylsodium yields were only 32% in a similar reaction but without any oxygen.

Inventive Example 5

The procedure of Example 4 was followed, in which amylsodium was prepared from a sodium dispersion (ethylbenzene dispersant) and amylchloride. In this reaction mixture were present 0.1 mol amylsodium and about 23 mols ethylbenzene. A gas containing air and nitrogen at a ratio of 1:1 was introduced into the reaction mixture while the latter was stirred at room temperature, the amount of oxygen being held at 0.001 mol. Reaction was continued at 90° C. for 3 hours, until there was obtained 68% yield of the following product:

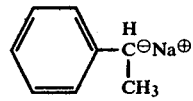

This yield was only 21% where no oxygen was used.

Inventive Example 6

0.1 mol amylsodium was prepared from the reaction of a sodium dispersion (n-octane dispersant) and amylchloride. To the resulting amylsodium was added 1 mol diphenylmethane. While the admixture was stirred, there was introduced at room temperature such amounts of air which correspond to 0.0005 mol oxygen. Reaction was continued at 40° C. for 30 minutes, until there was obtained 95% of the following product:

This yield was 78% in a similar reaction at 60° C. and for a period of 30 minutes but without the use of oxygen.

What is claimed is:

1. A transmetalation process which comprises reacting an organoalkali metal compound represented by the general formula:

RM where R is a hydrocarbon residue having a carbon number of 1 to 20 and a pKa value of RH exceeding 21, and M is an alkali metal selected from the group consisting of sodium, potassium, rubidium and cesium; with an hydrocarbon compound represented by the general formula:

R'H where R' is an organic residue having a carbon number of 1 to 20 and a pKa value of R'H exceeding 21 but lower than the pKa value of RH and adding 0.01–10 moles % based on said organoalkali metal compound of oxygen whereby an organoalkali metal of the general formula R'M is produced.

2. The process of claim 1 wherein said organometal compounds are selected from the group consisting of butylsodium, amylsodium, phenylsodium, butyllithium, butylpotassium and diphenylmethylpotassium.

3. The process of claim 1 wherein said hydrocarbon compounds are selected from the group consisting of toluene, xylenes, cumene, diphenylmethane, triphenylmethane, fluorene and indene.

* * * * *